(12) United States Patent
Farrar (10) Patent No.: US 12,138,097 B2
(45) Date of Patent: *Nov. 12, 2024

(54) DEVICE AND METHOD FOR PERFORMING MEDICAL IMAGING

(71) Applicant: CFL Research and Development, L.L.C, Springhill, LA (US)

(72) Inventor: Kelly Farrar, Springhill, LA (US)

(73) Assignee: CFL Research and Development L.L.C., Springhill, LA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/090,850

(22) Filed: Dec. 29, 2022

(65) Prior Publication Data

US 2023/0138707 A1 May 4, 2023

Related U.S. Application Data

(63) Continuation of application No. 14/993,498, filed on Jan. 12, 2016, now Pat. No. 11,576,641.

(51) Int. Cl.
*A61B 6/42* (2024.01)
*A61B 6/00* (2006.01)
*A61B 6/46* (2024.01)

(52) U.S. Cl.
CPC .......... *A61B 6/5258* (2013.01); *A61B 6/4258* (2013.01); *A61B 6/461* (2013.01);
(Continued)

(58) Field of Classification Search
CPC ..... A61B 6/037; A61B 6/4241; A61B 6/4258; A61B 6/461; A61B 6/481; A61B 6/5205;
(Continued)

(56) References Cited

U.S. PATENT DOCUMENTS 5,719,401 A 2/1998 Chaney et al.
5,818,050 A * 10/1998 Dilmanian ............. A61B 6/037
250/363.04
(Continued)

FOREIGN PATENT DOCUMENTS

WO WO-2015189603 A1 12/2015

OTHER PUBLICATIONS

D. Xu and Zhong He, "Gamma-ray energy-imaging integrated deconvolution," IEEE Nuclear Science Symposium Conference Recrod, 2005, pp. 882-886. (Year: 2005).*
(Continued)

*Primary Examiner* — Joseph M Santos Rodriguez
*Assistant Examiner* — Maria Christina Talty
(74) *Attorney, Agent, or Firm* — D. Tiller Law PLLC; Don Tiller (57) ABSTRACT

Gamma cameras may be used to obtain two-dimensional images of an emitting object, of which the most common form is the "Anger-type" gamma camera. The primary components in a conventional Anger-type gamma camera include, but are not limited to: a plurality of photo-multiplier tubes, a scintillator material, and a collimator. The disclosed invention claims a novel use of a gamma camera which eliminates the collimator. The new method is a method of forming an initial image from the incident radiation, which does not depend on any mechanical or other means of restricting the incident radiation to be passed on to a position-sensitive radiation detector. This method then uses mathematical deconvolution to produce an image of the object without the need for a collimator and without reliance on a pre-existing image.

27 Claims, 4 Drawing Sheets

(52) U.S. Cl.
CPC ............ *A61B 6/481* (2013.01); *A61B 6/5205* (2013.01); *A61B 6/547* (2013.01)

(58) Field of Classification Search
CPC ....... A61B 6/5258; A61B 6/542; A61B 6/547; G01T 1/1647
See application file for complete search history.

(56) References Cited

U.S. PATENT DOCUMENTS

| | | | | |
|---|---|---|---|---|
| 5,841,140 | A | * | 11/1998 | McCroskey ......... A61B 6/4258 250/363.04 |
| 7,840,052 | B2 | | 11/2010 | Zhao et al. |
| 8,008,625 | B2 | | 8/2011 | Subbarao |
| 2012/0032086 | A1 | | 2/2012 | Daghighian |
| 2013/0181990 | A1 | | 7/2013 | Rodenberg. et al. |
| 2014/0119495 | A1 | | 5/2014 | Jang |
| 2014/0249402 | A1 | * | 9/2014 | Kimchy ................. A61B 5/064 600/436 |

OTHER PUBLICATIONS

D. Xu and Zhong He, "Gamma-ray energy-imaging integrated deconvolution," IEEE Nuclear Science Symposium Conference Record, 2005, pp. 882-886 (2005).

Katherine L. Walker et al., "Un-colimated single-photon imagin system for high-sensitivity small animal and plant imaging," Jan. 7, 2015, Phy. Med. Biol. 60(1), pp. 403-420, (2015).

G.R. Ayers, et al., "Iterative Blind Deconvolution"; Optics Letters; 13, 547 (1998).

A.S. Carasso, et al., "Direc Blind Deconvolution"; SIAM J. Appl. Math.; 61 1980 (2001).

R. Vio, et al.; Dealing wtih Edge Effect in Least-Squares Image Deconvolution Problems; Astronmy and Astrophysics, 442, 397 (2005).

* cited by examiner

DEVICE AND METHOD FOR PERFORMING MEDICAL IMAGING

CROSS-REFERENCE TO RELATED APPLICATIONS

This application is a continuation of U.S. Nonprovisional application Ser. No. 14/993,498 entitled "DEVICE AND METHOD FOR PERFORMING NUCLEAR IMAGING" filed on Jan. 12, 2016, which is incorporated herein by reference in its entirety and for all purposes.

BACKGROUND

The present invention relates to the field of nuclear medical imaging. By replacing stable atoms in certain biological compounds with a radioactive isotope (i.e., a radioisotope) of the atoms, and then introducing such a radioactively "tagged" compound into a patient, radiation detectors and techniques used for research in nuclear physics can be used to observe the transport, accumulation, and elimination of these compounds—called "radiopharmaceuticals" within the body. The use of radiopharmaceuticals with associated techniques of detecting their emitted radiations in the context of medical studies and treatments falls under the description "nuclear medicine." However, these technologies used for nuclear medical imaging may also be used for non-medical purposes which include the imaging of non-biological objects. For medical imaging, the detected radiation is commonly in the form of gamma rays. For non-medical applications, any radioactive material may be the source of radiation, and other types of radiation may be used for imaging purposes.

There are a number of technologies in use for detecting gamma rays for the purpose of producing medical images. One of the most well-established and widely used devices is the gamma camera. Gamma cameras may be used to obtain two-dimensional (2D) images of an emitting object. Specifically, these images are projections of the emitting object onto a 2D surface. Moving the camera to different positions around the emitting object results in a set of image data to which it is possible to apply mathematical operations to obtain a three-dimensional (3D) image of the emitting object. This method of obtaining a 3D image is referred to generally as Single Photon Emission Computed Tomography, or "SPECT". The 2D images are typically projections onto a 2D plane and so are often called "planar" images, however, projections onto nonplanar surfaces are also possible.

Although the term "gamma camera" can include a fairly broad range of technologies capable of producing images of gamma ray sources, it is most commonly used in reference to Anger-type gamma cameras. As used herein, the term "Anger-type gamma camera" is meant to refer to gamma cameras which operate using the same basic principles of the Anger camera developed by H. O. Anger, as disclosed in U.S. Pat. No. 3,011,057, but also including the various modifications that have been adopted since that time. The primary components in a conventional Anger-type gamma camera include, but are not limited to: a plurality of photomultiplier tubes ("PMT"s), a scintillator material, and a collimator. In some recent Anger-type gamma cameras, the PMTs are replaced with solid-state devices.

Because of the relatively high frequency and energy of gamma rays, conventional refractive lenses cannot be used to form images in the gamma camera. Instead, in conventional gamma cameras, images are formed using collimation. Collimation is conventionally achieved by use of the collimator, which is typically a piece of gamma-ray absorbing material with a number of small through holes to allow passage of gamma rays travelling on a line approximately collinear with the axis of a hole. The collimator serves to restrict the angle of incidence of the detected gamma rays, thereby acting as the means of image formation. Once the image has been formed, various image processing methods may then be applied in an effort to improve the quality of the image. For conventional gamma cameras a position-sensitive gamma-ray detector provides a means by which an image is converted to signals which then may be digitized and stored. In contemporary conventional gamma cameras, this may be done first by digitizing the signals and then processing them by some other means such as a programmable computer or firmware. The total number of photons contributing to any point in the image is limited by the duration of exposure to the photon source, whether it is a source of visible light or of gamma rays.

The collimator is a primary limiting element in the performance of conventional gamma cameras. This is a fundamental consequence of a process by which collimators form an image. Spatial resolution of the image formed by the collimator is directly related to collimator hole size, and thus to collimator transmission efficiency. Large values of spatial resolution will correspond qualitatively to poorly resolved image details, while small values of spatial resolution correspond will correspond to well resolved image details. Therefore, improvement of the image resolution comes at the cost of the collimator transmission efficiency.

Other problems associated with the collimators are those of scattering and incomplete absorption. Ideally, only those gamma rays which pass directly unimpeded through the holes of the collimator contribute to the image. In practice, some gamma rays will be scattered off of the sides (the "septa") of the collimator holes into the gamma-ray detector, and some will pass through the sides into the detector. Both of these cases result in degradation of the image formed by the collimator on the gamma-ray detector.

An additional issue with the use of collimators is the need for a mono-energetic gamma source. Since the attenuation length and scattering probabilities in a material are strongly dependent on gamma-ray energy, collimators are designed for gamma rays of a specific energy. This in turn means that the choice of radioisotopes is limited to those which emit essentially mono-energetic gamma rays so as to avoid further deterioration of image quality. This restricts choices when designing radiopharmaceuticals for imaging different biological processes and restricts the possibilities for the development of improved gamma-ray detector technologies for use in gamma cameras.

Last, "low energy" collimators are fragile because they have very thin septa. Low energy collimators are preferred for use with 99 mTc, which is one of the most commonly used radioisotopes for medical imaging, but various trade-offs require the use of a collimator with thicker septa resulting in reduced image quality.

Previous approaches towards elimination or considerable reduction of the transmission efficiency limitations imposed by the presence of a collimator can be divided into two general categories. The first involves detector hardware and physical arrangements which are substantially different from conventional gamma cameras based on the Anger camera. These approaches tend to be significantly more expensive than traditional Anger-type gamma cameras. The second category involves measurements of gamma flux data over a volume of space rather than the conventional 2D time-integrated flux data, and in addition to flux data requires, among other things, some combination of: one or more 3D data sets unrelated to flux data, what is likely a very time-consuming use of diagnostic equipment to generate per patient modeling data, and a considerable amount of computation involving 3D matrices. Though a large amount of effort has been applied over many years towards addressing the limitations imposed by the necessity of the collimator in conventional gamma cameras, no alternative has been put into wide use. The conventional Anger-type gamma camera with a physical collimator is still the most widely used type of gamma camera primarily due to the low component cost, ease of construction, and ease of use as compared to other alternatives.

SUMMARY OF THE INVENTION

The present invention addresses the problems of prior technologies. The invention utilizes a position-sensitive radiation detector ("PSRD") to obtain a measurement of a time-integrated radiation flux distribution from which an image of a radiation source may be obtained. The radiation source may be a distribution of a radiopharmaceutical within a patient's body, the radiopharmaceutical having been administered to the patient by any conventional means. The radiation source may also be any other radiation source of interest; for example, sources in the industrial context. The PSRD produces a set of position data for incident radiation which includes, or from which may be obtained, a time-integrated radiation flux distribution over an active region of the PSRD. The PSRD may be one or more position-sensitive gamma-ray detectors suitable for use with a gamma camera, or it may be any other type of PSRD as appropriate for the type of radiation emitted from the source.

The time-integrated radiation flux distribution from the PSRD is used with a procedure to solve an integral equation describing a relation between the flux distribution, a response function, and the radiation source, to obtain an image of the radiation source. In one embodiment, a suitable response function may be supplied as input to a deconvolution procedure. In an additional embodiment, the response function may be described by a set of parameters and the resulting parameter space searched in conjunction with a procedure to solve the integral equation to find the appropriate response function as part of obtaining the image of the radiation source. In another embodiment, a myopic or semi-blind deconvolution procedure may be used in which only some of the characteristics of a response function are supplied. In another embodiment, the integral equation may be solved using other methods. In the preferred embodiment, a deconvolution procedure is used to compute an approximation of a projection of the radiation source onto the PSRD which can be used as a 2D image of a projection of the radiation source. Unlike previous uses of deconvolution techniques to enhance images taken with the conventional Anger-type gamma camera, this method does not require a previously captured image, but rather is a method for initial formation of the image.

A key advantage of this invention is that the image may be formed without the use of a collimator, thereby eliminating problems associated with the collimator's use. One result is that for medical applications, the levels of radiation that a patient is exposed to may be reduced while simultaneously improving the quality of the image obtained. Indeed, when a collimator is used, it is necessary to administer large amounts of radiopharmaceuticals to the patient to ensure enough gamma rays will be emitted and passed through the collimator. Another advantage of the invention is that, compared to conventional methods including collimators, there is no fundamental geometric limitation which necessarily results in a deterioration of spatial resolution with increasing source-to-detector distance. A further advantage is that no additional or more complicated gamma-ray detection hardware is necessary beyond what is found in a conventional Anger-type gamma camera, and the method may be used with data collection procedures that are conventionally used with Anger-type gamma cameras in obtaining planar or 3D images.

Images produced by the disclosed methodology and device may, for example, be used directly in planar imaging studies, combined via computed tomography methods to form 3D object images, or further processed in any of the conventional ways such images may be processed. Thus, these images may be used in place of images obtained from conventional gamma cameras that make use of collimation. The present invention is not limited to gamma cameras and nuclear medicine; rather, it may be applied to various technologies and applications that involve obtaining images from position-sensitive radiation detectors in general.

DETAILED DESCRIPTION OF THE INVENTION

This disclosure uses four terms of art that are defined as follows:

Position-Sensitive Radiation Detector ("PSRD"): A PSRD is defined as a device which provides a measure of the position at which radiation interacts with the detector. It may provide information about detection of radiation (photons or particles with mass) individually or collectively. Typically, PSRDs provide position information with respect to a 2D coordinate system relative to some physical location on the PSRD, but other types of PSRDs are also included.

Irradiance: Irradiance is used as conventionally in physics, specifically optics, to mean the amount of light falling on a surface as a function of position on that surface, having dimensions of power per unit area, and further understood to include particle radiation incident on a surface as a function of position on that surface so that the dimensions of irradiance may also be expressed as counts per unit time per unit area. Particle radiation is also understood to include both massless particles and particles having mass. The term "radiation" is understood to include particle radiation.

Flux: Flux is the irradiance integrated over an area. A flux distribution then, as a function of position and in the continuous limit with infinitesimal area elements, is the irradiance. It also follows that a discrete representation of irradiance corresponds to the flux as a function of position over an array of non-infinitesimal area elements. Flux has dimensions of power, and in terms of particle radiation the dimensions of flux may be expressed as counts per unit time. Flux integrated over time then, has units of energy, or in terms of radiation, units of counts.

Image: In the context of nuclear medical imaging, and radiation imaging in general, the term "image" is used somewhat more narrowly and colloquially than in the field of optics. Herein, "image" is taken to mean a readily intelligible representation of some physical and spatial attribute of an object. For an image to be readily intelligible, it may require that the observer have some familiarity with the nature and subject of the image. It is also to be understood that intelligible images may be blurred or distorted to some degree. This meaning of "image" is understood to include numerical representations of the image such that a digital representation of an image is also considered to be an image. It is also to be understood that "image" is not limited to 2D images and may include 3D images. In nuclear medical imaging, an "image" may be, for example, a readily intelligible representation of a distribution of radio isotope activity within a patient, or some part of a patient, or projections of that activity. This use of the term "image" also applies to imaging of radioactive sources in industrial contexts and other applications.

Figure 1:
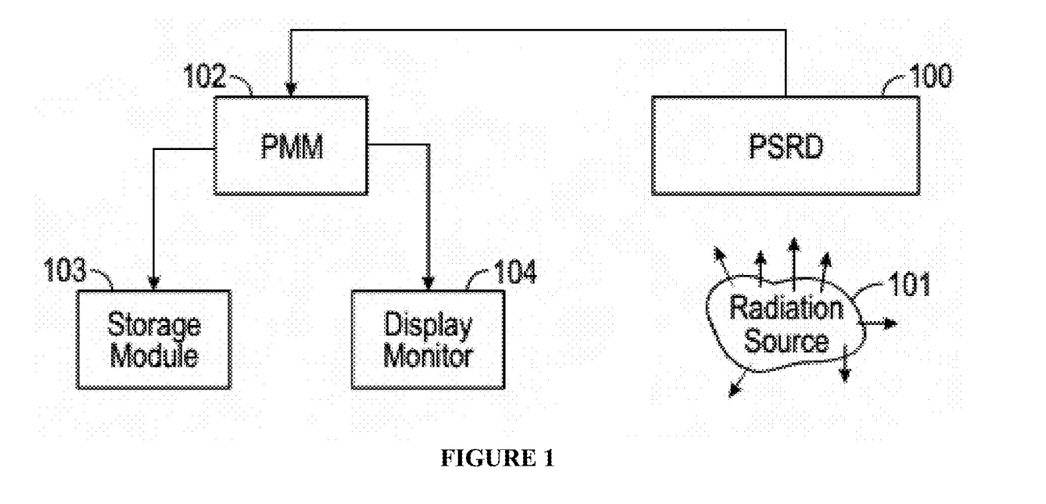
FIG. 1 is a diagram illustrating the preferred embodiment of the nuclear medical imaging system.

The preferred embodiment of the disclosed apparatus depicted in FIG. 1 comprises a PSRD 100 to be used in a way such that its active region is exposed to radiation source 101 to be imaged or a part of the radiation source 101 to be imaged. The active region of a PSRD is the part of the PSRD with which the incident radiation interacts in a way which allows the PSRD to detect it. For example, in a scintillation-based detector, the active region comprises at least a scintillator. In particular cases, the active region may be referred to as the active area. In this embodiment, the PSRD 100 is a position-sensitive gamma-ray detector ("PSGD") as may be found in conventional Anger-type gamma cameras. The PSGD may be kept stationary relative to the radiation source 101, or alternatively may be mounted so that it can be moved relative to the radiation source 101 in order to collect data needed for images of different projections, or for different approximations of a given projection, of radiation source 101 either independently or for other applications. The PSGD may also be moved in such a way as to collect data to be combined for other purposes such as effectively increasing the area of the PSGD active region. In an additional embodiment, a plurality of PSRDs may be used. In some embodiments it may be desirable to limit the exposed portion of the active region of the PSRD 100 or to block a part of the radiation source 101 from the view of the PSRD 100 by use of a mask. This is different from a collimator or other image forming means which has as a defining characteristic that it substantially modifies the angular distribution of radiation incident upon it.

In an additional embodiment, the PSRD 100 may be a PSGD in which light detection from a scintillator is performed using photodiodes rather than PMTs. In another embodiment, the PSRD 100 may be a PSGD in which one or more silicon-strip detectors are used in place of a scintillation arrangement. In yet another embodiment, the PSRD 100 might be an x-ray detector, a multi-wire proportional counter, a Cadmium Zinc Telluride detector, or any other type of radiation detector which exists or may be developed, and which can be used as a PSRD in any number or range of applications and industrial contexts.

In the preferred embodiment depicted in FIG. 1, the radiation source 101 may be a distribution of a radiopharmaceutical or other radioactive substance within the body of a patient. How the source of radiation came to be in the patient's body is not relevant. It could be a radiopharmaceutical or a metabolized product of a radiopharmaceutical. It could also be the result of intentional or accidental inhalation or ingestion of radioisotopes such as 131I, 15O, 18F, or 137Cs, or some type of radioactive object. In another embodiment the radiation source 101 could be a distribution of some radioactive material within an object or material of interest in an industrial process. Other embodiments and applications for this invention could involve imaging of other radiation sources, as well as types of radiation other than gamma rays.

In the preferred embodiment, the PSRD 100 detects gamma rays emitted by the radiation source 101 and produces signals related to the position of their incidence. After the initial processing of signals, a digitized version of the signals is then read out to a processor and memory module ("PMM") 102. In other embodiments, more or less signal processing can be performed internally or externally to the PSRD depending on the capabilities of the particular PSRD, and the more or less processed signals may be read out by the PMM 102 or stored in a storage module 103 for further processing at a later time.

The readout of information, in the form of signals or otherwise, from the PSRD may be carried out using a readout circuit which can be realized in many different ways. For example, the information could be transferred by use of a set of wires, a custom electrical signal bus, a standard RS-232 serial line, a USB serial line, a GPIB parallel line, an optical transfer coupling, a system involving a host-server scheme, or any other suitable method of transferring signals, data, or information between a particular choice of PSRD and a particular choice of PMM. As an example, a PSRD built with an RS-232 port could be connected to a PMM with an RS-232 port.

The PMM, with additional purposes to be further described, can also be realized in many different ways. For example, it could be a general-purpose programmable computer which has had a set of instructions incorporated into it by placing the instructions in memory, or specialized computation and processing hardware built for the purpose of carrying out the set of instructions incorporated into the layout of the circuitry, or a programmable computer with hardware optimized for the operations needed in the set of instructions, or a graphics processing unit based system.

The set of instructions can comprise a realization of parts of a method for image formation, described later, which may be carried out using a PMM, and could, for example, be in the form of a computer language, logic circuit design, or some other form, which the PMM could carry out. Incorporation of such set of instructions into a PMM produces a machine which can be used as a means in implementing the referred to method of image formation.

Although processors include memory, the memory component of a processor and memory module could additionally be realized in many ways, including use of solid state, magnetic, optical, or any other suitable type of memory device which could be used for information storage and retrieval. A storage module may be realized separately, or additionally, in the same way.

It will be apparent to those skilled in the art that there are many ways to implement each of, a readout circuit, a PMM, and a storage module, both known, and such as may be developed, which can be used to implement functions of the described embodiments which fall into the scope and spirit of the system and method being described.

A measure of the position of detected gamma rays is then computed by the PMM 102 using information from the PSRD 100. In another embodiment, position information might be obtained through use of analog circuitry before being digitized for readout to the PMM 102. In yet another embodiment, position information might be determined by firmware included with the PSRD 100 before being passed to the PMM 102 or position information might be computed using the field-programmable gate arrays included with or external to the PSRD 100. It should be understood that there are many other ways in which the processing of signals from a PSRD may be accomplished so that the position information about the detected radiation is available for further processing.

In the preferred embodiment, energy information about the detected gamma rays is then read out to the PMM 102. In other embodiments, energy information may be read out, and may be processed more or less by circuitry internal or external to the PSRD 100 or by the PMM 102. Energy or other information obtained from the PSRD 100 may be used to discriminate among position and other information provided by the PSRD 100. Such discrimination is useful for several purposes, including reducing the contribution of background gamma rays and gamma rays that have been scattered after being emitted.

The PSRD 100 collects data until one or more sufficiency criteria are met. In the preferred embodiment, a predetermined number of counts are used as a sufficiency criterion. The resulting data set comprises a time-integrated radiation flux distribution ("TRFD") data set and is a measure of irradiance of the radiation source 101 or a part of the radiation source 101 in which the angular distribution of the radiation incident on the PSRD and contributing to the measure of irradiance is substantially unmodified from the angular distribution of the radiation at points near to, but outside of, the source of radiation or part of the source of radiation. Thus, in the preferred embodiment, the presence of a collimator or other image forming device is undesirable. In other embodiments, the TRFD data set may meet other sufficiency criteria. For example, data may be collected until a measure of the statistical noise describing the data satisfies some threshold. Information about the data including graphical representations of aspects of the data as well as results based on the data may be shown on display monitor 104. Detector-artifact corrections may be applied to the TRFD data set using conventional methods which are known in the art. Flood-field measurements may be carried out in a manner analogous to that used with a conventional Anger-type gamma camera. However, in the absence of a collimator, it may be desirable to reduce the activity of the radiation source used for flood-field measurements. In the preferred embodiment, flood-field measurements may be carried out using a planar radiation source. Other embodiments may use other source geometries and make appropriate geometric compensation. Once a sufficient TRFD data set has been obtained, corrections for detector artifacts, such as position-dependent efficiency variations, non-linearities, and energy dependent efficiency variations, may be applied. Alternatively, one or more such corrections may be incorporated into a method of image formation described below. At this point a method of forming an image from the data may be applied or the data may be stored for later use.

The novel method of image formation begins with a TRFD data set. This data set represents a region of a section of a virtual 3D TRFD associated with the radiation source 101, obtained from an active region of the PSRD 100, and may include detector-artifact corrections and smoothing or filtering to reduce effects of noise. A 3D radiation flux distribution may be thought of as a 3D convolution of the spatial distribution of activity in the radiation source 101, and a second 3D function, which may be thought of conceptually as analogous to a transfer function or to a response function. This second 3D function may be further understood by rough analogy with either a point spread function or an impulse response function. However, neither the term "point spread function" nor the term "impulse response", given their usual application and definitions, may be strictly correct as applied in this situation. Herein, the more general term "response function" ("RF") is being used with the understanding that it includes any function derived from one or more response functions, and further understood to include any function which, along with a function that at least approximately represents the image of the source of radiation 101 or a part of the source radiation 101, may comprise an integrand in an integral equation described below. The convolution may be understood as an integral equation so that the RF may also be referred to as a kernel or kernel function. It can be shown that a projection of a convolution of two three-dimensional functions into two dimensions is equivalent to a convolution of projections of the two three-dimensional functions into two dimensions. Given a projection of a 3D RF into two dimensions and a corresponding projection of a virtual 3D TRFD data set, it is possible in principle to solve for a projected image of the radiation source 101. However, a projection of a virtual 3D TRFD data set is not generally available. What is available is a bounded slice of the 3D TRFD data set. It has been found under certain conditions, such a slice can be at least approximately described by a related integral equation. More specifically, the integral equation approximately relates the irradiance via the TRFD data set to an integral comprising a product of a RF that can be approximately related to the response of the PSRD to a distribution of radiation, and an image function that approximately describes a 2D projection image of the radiation source 101 or a part of the radiation source 101. Given a 2D RF or a suitable approximation, the integral equation may then be solved to obtain an approximation of the projected image of radiation source 101 or a part of the radiation source 101. This method of image formation makes use of an angular distribution of radiation emitted from the radiation source 101 as opposed to other methods, such as collimation for example, which form an image by modifying the angular distribution of incident radiation. Portions of the radiation may also be used provided that the angular distribution of such portions remains sufficiently unmodified. In situations where the particulars of the RF are unknown, but the RF and the image are sufficiently constrained it is possible to solve for both the RF and the projected image.

The method of image formation involves an RF and solution of an integral equation. If a suitable RF is known or can be obtained then the integral equation may be solved with that RF. Alternatively, a suitable RF may be found in conjunction with the solution of the integral equation. This may be done in a number of different ways.

For purposes of explaining the method of image formation, a preferred embodiment will be described, first describing a method of solving the integral equation for a given RF, and then providing some examples of ways to obtain a suitable RF. This method of description, as well as the particular embodiment described, is intended as a way of describing the principles of the method of image formation by way of example. It will be apparent to those skilled in the art that there are other ways of implementing the method of image formation which fall within the scope and spirit of the method of image formation being described.

Figure 2:
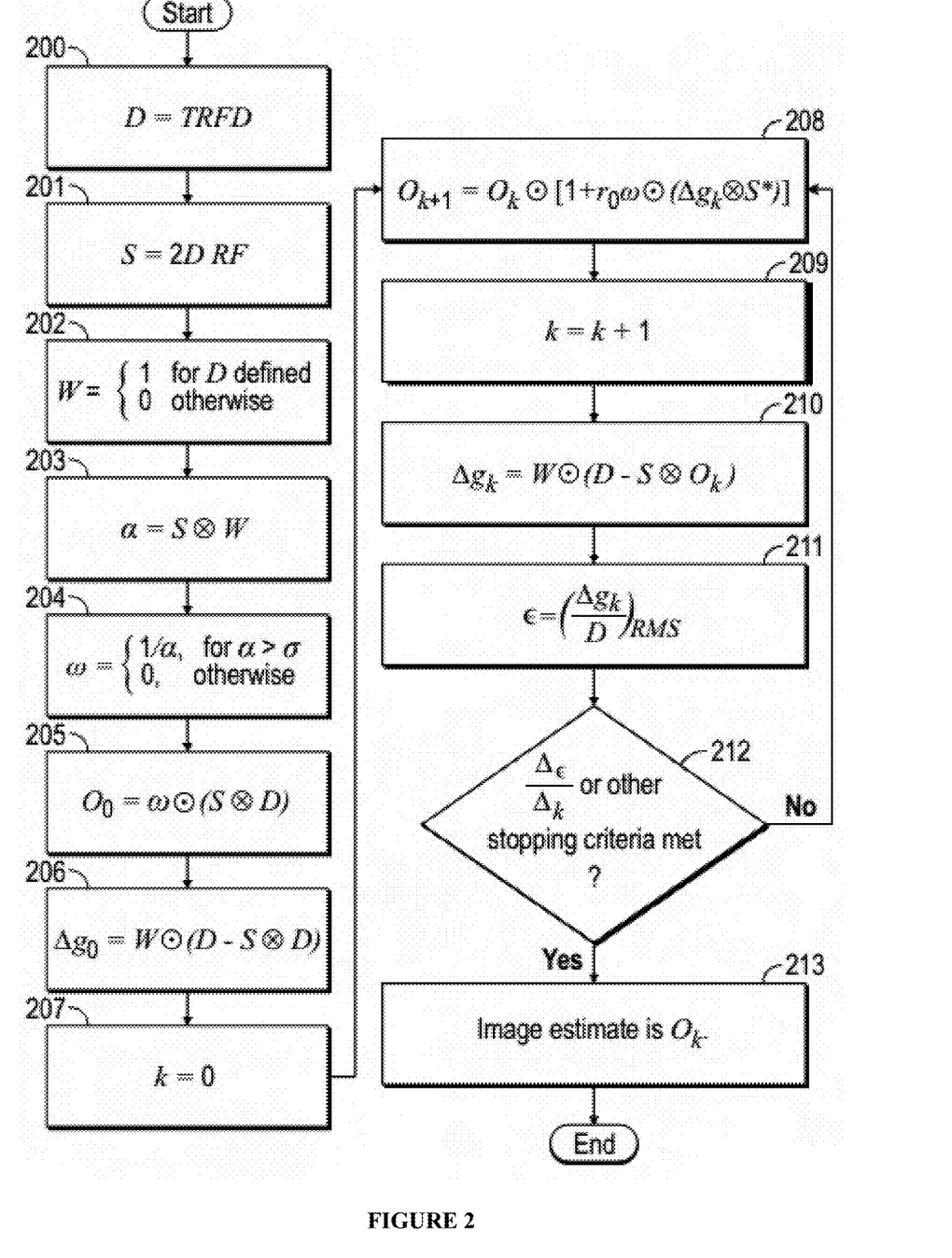
FIG. 2 is a simplified flowchart illustrating an exemplary process for solving an integral equation suitable for use in image formation.
Figure 3:
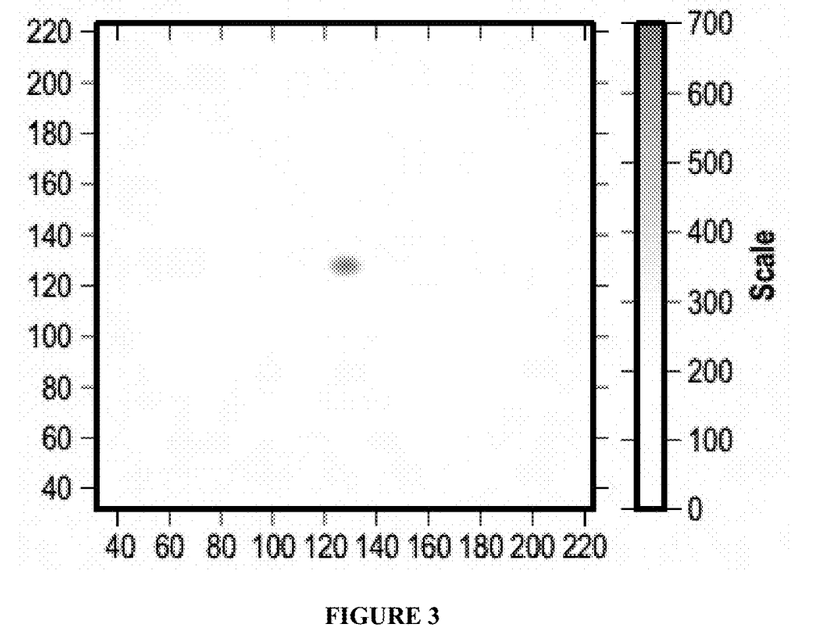
FIG. 3 is a projection onto two dimensions of a 3D object to be imaged. The object is an ellipsoid with a diffuse surface.
Figure 4:
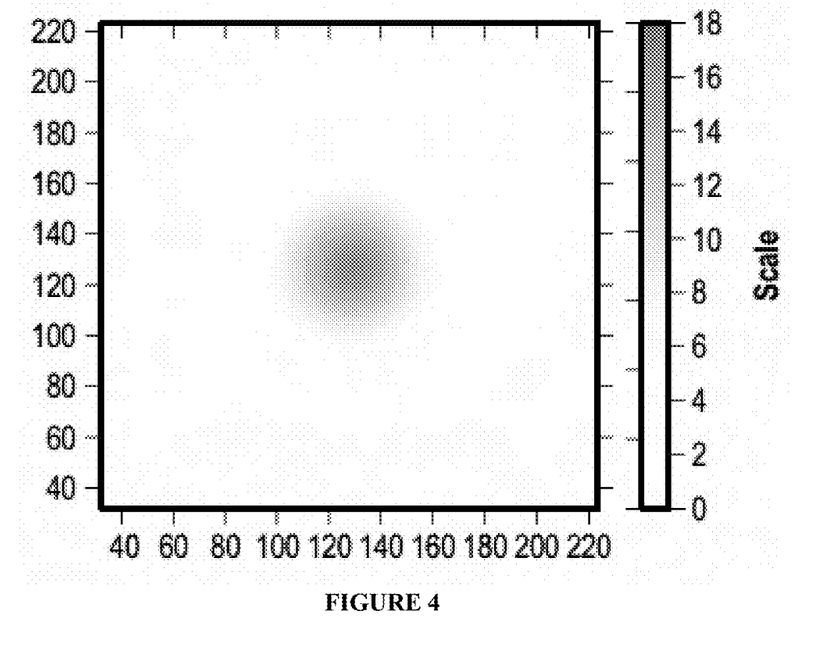
FIG. 4 discloses the result of a simulation of data collected by a position-sensitive gamma-ray detector exposed to the object in FIG. 3. Internal scattering at the source and detector artifacts (other than detector resolution) are not included because such effect can be handled by the same methods currently in use. This figure essentially shows what would be seen if the collimator or other imaging mechanism were removed from the Anger-type gamma camera, and the remaining detector were exposed to the object of FIG. 3.
Figure 5:
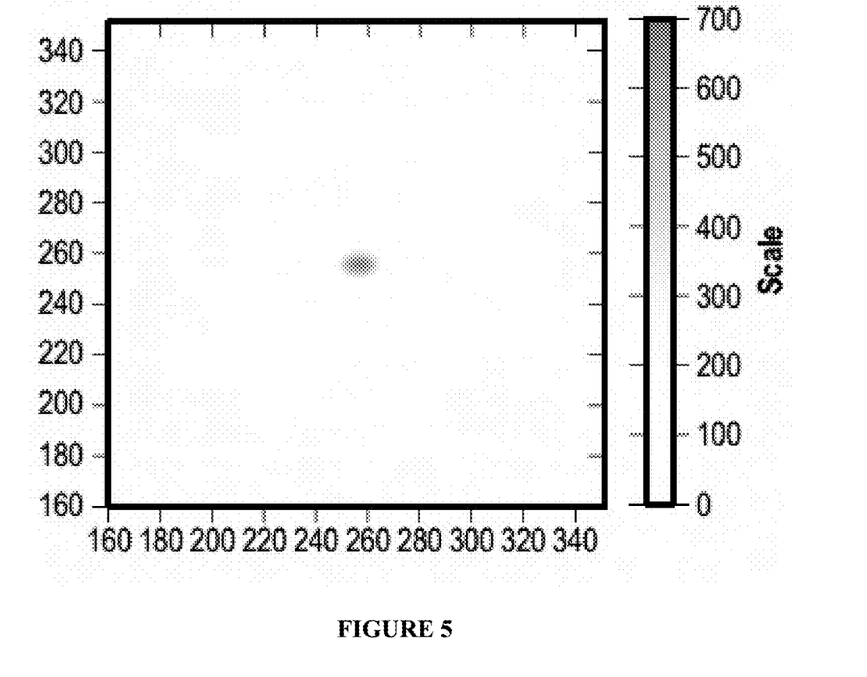
FIG. 5 is the image produced from the data of FIG. 4 using the method described herein. The image produced is an image of the object in FIG. 3.

FIG. 2 provides a simplified flow chart illustrating the preferred embodiment of a solution of the integral equation suitable for use in the method of image formation. It is desirable that an iterative method of solution, such as the one illustrated, be sufficiently stable in the presence of noise that iterations may be continued until an acceptable solution is obtained. Other methods, including non-iterative methods, could be used so long as they are either sufficiently robust in the presence of noise or so long as noise can be filtered sufficiently to allow a particular method to yield an acceptable solution. The solution method exemplified in FIG. 2 may preferably be carried out using the PMM 102, or by use of a separate processor means.

In this embodiment, solution of the integral equation begins with initialization of certain objects. At block 200, an object D, which represents any suitable representation of the TRFD data set, and which may have been corrected for detector artifacts, is initialized. At block 201 an object S, is initialized to a representation of a RF corresponding to a kernel function in an integral equation as referred to above. In this preferred embodiment the RF is a 2D RF and the object S may be a representation of the 2D RF or an appropriate approximation to the 2D RF. The object D may be a TRFD data set obtained from PSRD 100. Further, the object D may be represented as an array with each element corresponding to a spatial position represented in the TRFD data set, or any other useful representation of the TRFD data set.

At block 202 a mask W is initialized by setting each element in the mask W corresponding to an element in the object D to one, and all other elements in the mask W to zero. In this embodiment, the mask W is large enough to accommodate a region outside that represented by the object D by at least the size of the space over which the object S is taken to be non-zero. In alternative embodiments, the mask W may be used, for example, as a weighting mask to include position-dependent detector corrections. In such cases, values other than one may be used to represent a position-dependent weighting.

At block 203 an object $\alpha$ is initialized to be a convolution of the object S and the object W. Variations of this embodiment may use different computational procedures as alternatives to conventional convolution operations here and in other steps. In the preferred embodiment, convolution may be implemented using a Fast Fourier Transform and multiplication in the spatial frequency domain; however, other computational procedures could also be used and in some situations might be preferable. Outside the boundary that encloses the region where the TRFD data set is defined, $\alpha$ falls to zero over a distance dictated by the details of the 2D RF. This boundary may correspond to a physical boundary of the PSRD 100, a TRFD data set boundary, or other useful boundaries. At block 204 an object $\omega$ is initialized to be $1/\alpha$ for $\alpha > \sigma$ and zero otherwise. This may be understood as being done element by element, meaning that each element in the object $\omega$ may be set to 1 divided by the corresponding element in $\alpha$, so long as the element in the object $\alpha$ is greater than $\sigma$. Otherwise, the element in the object $\omega$ is set to zero. $\sigma$ is a computational parameter chosen to specify a point on the tail of the 2D RF, and thus corresponds to a range outside the edge of the boundary beyond which a contribution to formation of the image within the boundary may be treated as negligible. The object $\omega$ is used in extrapolating the computation of the image to the region outside the boundary, allowing effects of the boundary on the computed image inside the boundary to be minimized.

At block 205 object $O_0$ is initialized to $\omega \odot (S \otimes D)$. The $\otimes$ represents a convolution operation, and $\odot$ represents an element-by-element multiplication. At block 206 object $\Delta g_0$ is initialized to $W \odot (D - S \otimes D)$, and at block 207 an iteration counter k is initialized to zero. Other variations of this embodiment may initialize objects $O_0$ and $\Delta g_0$ differently; for example, by using constant values.

Block 208 comprises an iteration step in which an object $O_{k+1}$ is computed from object $O_k$, and other previously initialized or computed objects, as $O_{k+1}=O_k\odot[1+r_0\omega\odot(\Delta g_k \otimes S(-r))]$. (Note that, $S(-r)$ transforms into the Fourier domain as the complex conjugate of the Fourier transform of S, where S is understood to be a function of a coordinate vector r.) In this embodiment, $r_0$ is a computational parameter which regulates a trade-off between numerical stability and rate of convergence of the computation. $r_0$ may be determined in practice by maximizing the rate of change of $O_k$ with respect to the iteration counter k, consistent with a continual and stable decrease in the Root Mean Square ("RMS") of the change in $O_k$. Alternatively, an upper limit on $r_0$ may be obtained from an analysis of the properties of an array representing S in the context of the specifics of the computational procedures used.

The iteration counter k is incremented at block 209. Block 210 comprises an intermediate computation in which an object $\Delta g_k$ is computed as $\Delta g_k = W \odot (D - S \otimes O_k)$. A variable $\varepsilon$, may be computed for use in monitoring progress of the computation at block 211 as $$\varepsilon = \left(\frac{\Delta gk}{D}\right)\text{RMS}.$$

Here $\varepsilon$ is computed by taking the RMS of $\Delta g_k$ scaled element by element by D.

As the computation progresses towards a solution, $\varepsilon$ tends toward some small value$\geq 0$. In this preferred embodiment the rate of change of $\varepsilon$, $$\frac{\Delta \varepsilon}{\Delta k},$$

is used at block 212 in comparison with some predetermined value, as a simplified example of a stopping condition. If this condition is not satisfied, then the iteration loop is repeated beginning with block 208. When the condition is satisfied, then the iteration loop is stopped at block 213 and $O_k$ may be taken as an estimate of the solution of the integral equation for the supplied RF. In additional embodiments, other quantitative or qualitative criteria may be used as alternative or additional stopping criteria. Further, operator experience and judgment as to the specific stopping criteria needed to produce a sufficiently satisfactory image with a particular embodiment as applied to a particular set of data may be used to adjust, replace, or augment stopping criteria.

In other embodiments, a noniterative, or direct, method of solving the integral equation could be used.

When the stopping condition, or criteria in other embodiments, is met, iteration stops. The object $O_k$ may then be taken as an estimate of the projected image of the radiation source 101 or part of the radiation source 101. This estimate then may be used as would any conventional image, or the estimate may be further processed by any conventional or other method of image processing. In another embodiment, if the RF were not satisfactorily well known then the RF could be modified, subject to constraints, in such a way as to produce a more satisfactorily suitable RF, S could be re-initialized, and the process illustrated by FIG. 2 repeated. In one embodiment the object S would be initialized to a representation of the modified RF at block 201, the steps of blocks 202, 203, and 204 would be carried out, and then processing would begin again at block 206 using the previously obtained $O_k$ as $O_0$, and $\Delta g_k$ initialized using the step of block 210 as $\Delta g_0$. In other embodiments the object $O_0$ might be initialized as previously at block 205. Yet other embodiments might use various results obtained with the previous RF to initialize some objects and not others. In still other embodiments, using a method of solving the integral equation different from that illustrated in FIG. 2, the initial RF would be replaced by an improved RF. Some ways of obtaining a suitable RF are described below.

The method of solving the integral equation just described has been found to be reasonably insensitive to statistical noise in the TRFD data set and to discontinuities as may occur at a boundary. Other embodiments of the method of forming an image from the TRFD data set may make use of some variation of an established procedure or some other procedure for solving an inverse convolution problem or more generally an integral equation as referred to previously. For example, a person having ordinary skill in the art may consider using a variation of the Landweber procedure, a myopic or semi-blind deconvolution technique, or a blind deconvolution technique.

The nature of the problem is such that acceptable image estimates may be obtained with a range of variation in the RF used with the method of image formation. In different embodiments, specifics of the RF parameters and to an extent the form of the RF may vary. Further, in some applications it may be desirable to consider different optimizations with regard to speed, efficiency, accuracy, and other considerations, which may be obtained by using various approximations to some ideal RF. Considering this variation, the following description is intended to illustrate a basis for, and some examples of, suitable approaches to the construction of a RF for use in the method of image formation. It should be understood that the nature of the equations to be solved, including numerical representations, is such that a variety of approaches can lead to a suitable RF. It will be apparent to those skilled in the art that there are many variations of what constitutes a suitable RF for use with the method of image formation and to approaches to the construction of such a suitable RF encompassed within the scope and spirit of the subject matter being described.

Conceptually, construction of a RF may begin with consideration of the irradiance of a point source on a plane. Consider a plane described by a Cartesian coordinate system in which the origin is located at the point closest to the point source. The distance from the point source to the plane may be taken as z, and the coordinates in the plane described by x, and y. Within the plane, distance from the origin is then given by $\rho$ where $\rho^2 = x^2 + y^2$. After normalizing over the plane, the normalized irradiance in the plane is given by:

$$h_N(\rho; z) = \frac{z}{2\pi(\rho^2 + z^2)^{3/2}} \quad \text{("Equation 1")}$$

This might be viewed as a 3D response function in $\rho$ and z except that there is a singularity at $\rho=0$, $z=0$. This singularity is a consequence of the point nature of the radiating source. If $h_N$ is viewed as a distribution, then as $z \to 0$, $h_N$ tends to a 2D polar delta function. If $h_N$ is projected over z onto the x-y plane the result also has a singularity at $\rho=0$. From the perspective of Fourier frequency space, a delta function in the spatial domain would require an infinite bandwidth in spatial frequency and so while it might be a useful approximation, this response function would be non-physical.

A PSRD has a finite spatial-frequency bandwidth which is limited by its spatial resolution, or from a different perspective, the spatial bandwidth corresponds to the spatial resolution. By convolving Equation 1 with a 2D Gaussian which represents the spatial resolution of the PSRD, one eliminates the singularity and obtains a more physically realistic RF. Projecting the result of this convolution over z from some lower limit $z_0 > 0$ to some upper limit $z_1 < \infty$ and normalizing, yields a RF which is suitable for use in the procedure illustrated in FIG. 2.

In view of the description surrounding Equation 1, it might be tempting to view parameters $z_0$ and $z_1$ or their equivalent simplistically as geometrical parameters. While such an approach may lead to a useable RF and may be used to begin a parameter search, it is otherwise likely to yield a less than optimal result.

There are many alternative ways to characterize or represent a RF. In addition, although Equation 1 provides some context for the development of an RF, RFs suitable for use in the method of image formation may also be obtained by purely empirical methods. In different embodiments an RF could be parameterized using other parameters. For example, one could use parameters more directly characterizing an RF such as its width and peak height, width and the ratio of peak height to width, or any other convenient or useful parameterization. In another embodiment one could obtain a suitable RF by assuming a RF in the form of a radially symmetric Lévy stable probability distribution to obtain a set of parameters from a Fourier transform of known representative images or of the TRFD data set. In other embodiments one might use any conventional or other blind deconvolution technique coupled with the procedure illustrated in FIG. 2 or with some other procedure for solving the integral equation. In still other embodiments one might use some type of myopic or semi-blind deconvolution method coupled with the procedure illustrated in FIG. 2 or with some other procedure for solving the integral equation.

In the preferred embodiment, an RF is formed by convolution of Equation 1 with a 2D Gaussian which represents the spatial resolution of the PSRD. The result is then integrated between limits $z_0 > 0$ and $z_0 + \Delta z$, where $\Delta z \equiv z_1 - z_0$; filtered with the same filter used to filter noise in the TRFD data set; and normalized. Values for $z_0$ and $\Delta z$ may be determined from a parameter search guided by any information available about the source distribution, or from previous experience imaging similar objects under similar conditions. The RF thus produced is suitable for use in initializing the object S in block 201 of FIG. 2, or for equivalent purposes in other embodiments. The RF obtained by this procedure could be refined by using it with a blind, myopic, or semi-blind deconvolution procedure.

In an additional embodiment when it is desirable to adjust the initial RF, a blind deconvolution method may be used as follows. By interchanging the objects S and O in the process illustrated in FIG. 2, and applying constraints to S, the modified process may be used to obtain an improved estimate of the RF. This improved RF may then be used again to initialize the object S at block 201 as previously described, and the process illustrated in FIG. 2 used again to obtain another estimate of $O_k$. When both objects S and $O_k$ satisfy a set of predefined stopping criteria, the process is stopped, and the object $O_k$ may be taken as an estimate of the projected image of the radiation source 101.

In an additional embodiment, a semi-blind or myopic deconvolution method may be used in which the RF is constrained to be radially symmetric. In another variation, the RF might be characterized by a sum of Gaussians with a set of Gaussian parameters being determined by a fit to the RF obtained from a blind, semi-blind or myopic process used with the process of FIG. 2. In this embodiment the set of Gaussian parameters would then be used to compute the new RF which would be used to initialize object S at block 201 of FIG. 2. In other embodiments other procedures for estimating an adjusted RF may be used. For example, a parameter search could be used in conjunction with a process such as that illustrated in FIG. 2, or with some other procedure for solving the integral equation. The results of the parameter search could then be used to obtain an adjusted RF which would then be used to obtain a new estimate for the object $O_k$.

Further variations or embodiments can be made for finding the desired RF. In one, a multiframe or multichannel blind deconvolution approach might be used in which a TRFD data set is collected from more than one position relative to the radiation source 101 in such a way that the same projection of radiation source 101 is to be imaged but different response functions would apply to the different TRFD data sets. This would allow additional constraints to be applied to the process of solving the integral equation for an estimate of the object $O_k$. In another embodiment, a plurality of 2D planar images of the radiation source 101 could be obtained from a plurality of angles or distances which could be used to provide additional constraints for use in solving the integral equation to obtain an improved estimate of the object $O_k$, an improved estimate of the RF, or both. A person having reasonable skill in the art could also find a suitable RF by using empirical or semi-empirical approaches.

The foregoing description has been presented for the purposes of illustration and description. It is not intended to be exhaustive or to limit the subject matter being described to the precise form disclosed. Other modifications may be possible in light of the above teachings. The preferred embodiment, variations, and other embodiments referred to, were chosen and described in order to best explain the principles involved and their practical application, so as to enable others skilled in the art to make best use of the subject matter disclosed in various embodiments and various modifications as are suited to the particular use contemplated. It is intended that the appended claims be construed to include other alternative embodiments except insofar as limited by the prior art.

In the specification and claims, unless the phrase "means for" or "step for" is specifically used, it is to be understood that the applicant does not intend to invoke section (f) of 35 U.S.C. section 112.

What is claimed:

1. A method for performing nuclear imaging of a radioactive material comprising:
   (a) placing a position-sensitive radiation detector so that the position-sensitive radiation detector is open to radiation emitted from a source of radiation or from part of a source of radiation so that the position-sensitive radiation detector detects a radiation incident from the source of radiation or part of the source of radiation;
   (b) the position-sensitive radiation detector is used in obtaining a measure of irradiance of the radiation emitted from the source of radiation or from part of the source of radiation;
   (c) wherein the position-sensitive radiation detector does not comprise a collimator;
   (d) wherein the measure of irradiance to be obtained involves at least one location external to the source of radiation or part of the source of radiation;
   (e) wherein radiation incident on the position-sensitive radiation detector and contributing to the measure of irradiance is uncollimated; and
   (f) solving an integral equation to obtain an image function which approximately represents at least a two-dimensional projection of the source of radiation or part of the source of radiation; and
   (g) wherein the integral equation approximately relates the measure of irradiance of the radiation emitted from the source of radiation or part of the source of radiation to an integral with an integrand comprising: a product of a response function that is approximately related to a response of the position-sensitive radiation detector to a distribution of radiation and the image function.

2. The method in claim 1 further comprising reducing a contribution of scattered radiation to the measure of irradiance of the radiation emitted from the source of radiation or part or the source of radiation.

3. The method in claim 1, wherein the measure of irradiance is expressed in a finite representation.

4. The method in claim 1, wherein the response function is expressed in a finite representation.

5. The method in claim 1, wherein the integral equation is solved by using a numerical deconvolution method.

6. The method in claim 5, wherein the numerical deconvolution method is a direct method.

7. The method in claim 5, wherein the numerical deconvolution method is an iterative method.

8. The method in claim 5, wherein the numerical deconvolution method is a blind, myopic, or semi-blind mathematical method.

9. The method in claim 5, wherein the numerical deconvolution method is a multichannel or multiframe method.

10. The method of claim 5, wherein the numerical deconvolution method assumes a radially symmetric response function.

11. The method of claim 1, wherein the response function is derived from integration over parameters of a response function approximately representing the response of the position-sensitive radiation detector to a point source of radiation.

12. The method of claim 1, wherein the source of radiation to be imaged results from a radioactive substance present in a patient in a context of medical imaging.

13. A device for creating images of radioactive material comprising:
    (a) at least one position-sensitive radiation detector;
    (b) a source of radiation;

(c) a readout circuit;
(d) wherein the position-sensitive radiation detector comprises at least one active region;
(e) wherein the active region of the position-sensitive radiation detector is external to the radiation source;
(f) wherein the position-sensitive radiation detector is open to incident radiation such that a measure of position of radiation incident on the position sensitive radiation detector comprises at least one measure of irradiance of the radiation emitted from the source of radiation or part of the source of radiation;
(g) wherein at least one position-sensitive radiation detector is open to incident radiation from the source that is uncollimated;
(h) wherein at least one of the position-sensitive radiation detectors does not comprise a collimator;
(i) wherein the readout circuit transfers information between at least one position-sensitive radiation detector and at least one processor and memory module;
(j) wherein the processor and memory modules are capable of solving the an integral equation to obtain an image function which approximately represents at least a two-dimensional projection of the source of radiation or part of the source of radiation;
(k) wherein the integral equation approximately relates the measure of irradiance of the radiation emitted from the source of radiation or part of the source of radiation to an integral with an integrand comprising: a product of a response function that is approximately related to a response of the position-sensitive radiation detector to a distribution of radiation and the image function.

14. The device of claim 13, wherein at least one position-sensitive radiation detector is oriented such that the radiation emitted from the radiation source is incident on the active region of the position-sensitive radiation detector.

15. The device in claim 13, wherein the response function is derived from integration over parameters of a response function approximately representing the response of at least one position-sensitive radiation detector to a point source of radiation.

16. The device in claim 13, wherein the radioactive material results from a radioactive substance present in a patient during medical imaging.

17. The device in claim 13, wherein at least one position-sensitive radiation detector is shielded to reduce the effects of radiation from sources other than the source of radiation.

18. The device in claim 13, wherein at least one position-sensitive radiation detector is capable of measuring the an energy of incident radiation.

19. The device in claim 13, wherein the representation of the image function is displayed on a display monitor.

20. The device in claim 13, wherein at least one position-sensitive radiation detector is mounted in a way that allows movement relative to the source of radiation.

21. The device in claim 13, wherein a plurality of position-sensitive radiation detectors are mounted in a way that allows for a measure of irradiance from the radiation source over an area greater than can be obtained with only one position-sensitive radiation detector.

22. The device in claim 13, wherein the integral equation is solved by using a numerical deconvolution method.

23. The device in claim 22, wherein the numerical deconvolution method is a direct method.

24. The device in claim 22, wherein the numerical deconvolution method is an iterative method.

25. The device in claim 22, wherein the numerical deconvolution method is a blind, myopic, or semi-blind mathematical method.

26. The device in claim 22, wherein the numerical deconvolution method is a multichannel or multiframe method.

27. The device in claim 22, wherein the numerical deconvolution method assumes a radially symmetric response function.

* * * * *